United States Patent [19]

Weete et al.

[11] Patent Number: 5,453,523
[45] Date of Patent: Sep. 26, 1995

[54] PROCESS FOR OBTAINING HIGHLY PURIFIED PHOSPHATIDYLCHOLINE

[75] Inventors: John D. Weete, Auburn, Ala.; George L. Griffith, Bethlehem, Pa.

[73] Assignee: Emulsion Technology, Inc., Parrish, Ala.

[21] Appl. No.: 77,684

[22] Filed: Jun. 16, 1993

[51] Int. Cl.⁶ .................................................. C07C 9/02
[52] U.S. Cl. ................................ 554/10; 554/80; 554/83
[58] Field of Search .................................. 554/83, 10

[56] References Cited

U.S. PATENT DOCUMENTS

| | | | |
|---|---|---|---|
| 4,235,793 | 11/1980 | Betzing | 554/83 |
| 4,528,139 | 7/1985 | Napp | 554/83 |
| 5,008,037 | 4/1991 | Weete et al. | 252/314 |

Primary Examiner—José G. Dees
Assistant Examiner—Dwayne C. Jones
Attorney, Agent, or Firm—Burns, Doane, Swecker & Mathis

[57] ABSTRACT

Provided is a process for removing non-choline phosphatides from a lecithin material to facilitate obtaining a highly purified phosphatidylcholine product which is essentially free of non-choline phosphatides. The product can be obtained efficiently and effectively, even when starting with a raw soybean gum (lecithin).

11 Claims, 1 Drawing Sheet

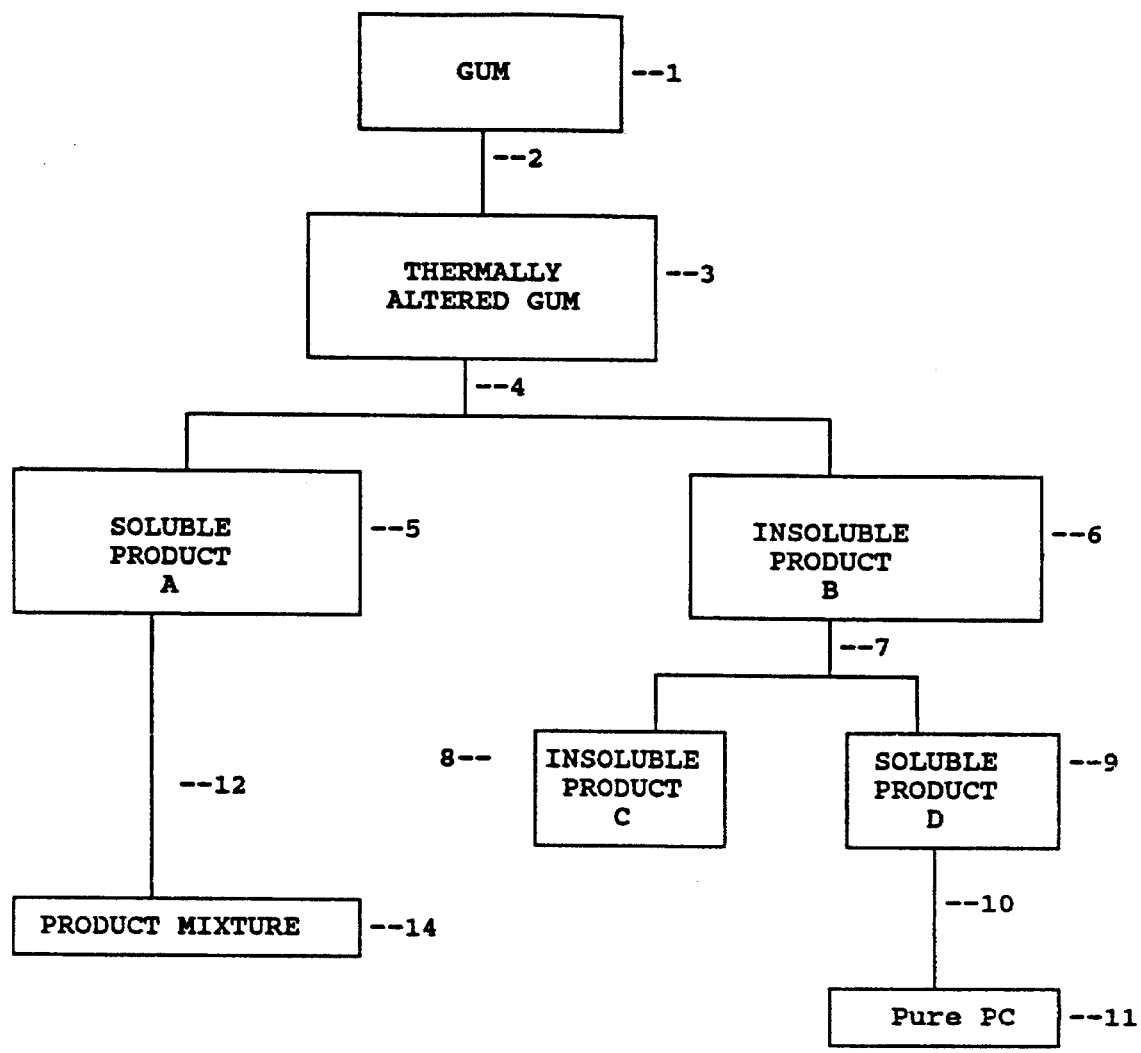
FIGURE

PROCESS FOR OBTAINING HIGHLY PURIFIED PHOSPHATIDYLCHOLINE

BACKGROUND OF THE INVENTION

The present invention relates to a process for obtaining purified phosphatidylcholine. The present invention in particular relates to a method for obtaining purified phosphatidylcholine which produces a mixture of glycerides as well. In another aspect, the present invention relates to a process for obtaining purified phosphatidylcholine from a raw lecithin gum.

In the fats and oils industry, the term "lecithin" is used to refer to a mixture of phosphatides that may include phosphatidylcholine (PC), phosphatidylethanolamine (PE) phosphatidylinositol (PI), phosphatidylserine (PS) phosphatidic acid (PA) and others. In the scientific literature, the term lecithin has been used to refer to PC, and the term "cephalin" has been used to refer to PE and mixtures of PE and the non-choline phosphatides. The industry use of the term lecithin is applied herein, and names for specific phosphatides (e.g. PC, PE, etc.) will be used as appropriate except when other patents and literature are quoted.

Processes for the separation of lecithin from contaminating substances are well known in the art. For example, see, Szuhaj, B.F. (ed.) Lecithins, American Oil Chemist's Society, Champaign, Ill. 1989. Recognition of the unique properties and possible uses of individual phosphatide components of lecithin, particularly PC, and the adverse effects in certain applications of contaminating non-choline phosphatides in PC enriched fractions, has stimulated the search for improved methods of PC purification from lecithin.

There are many known methods for obtaining purified phosphatidylcholines from various starting materials. For example, German Patent No. 1,617,679 discloses a process to obtain highly purified phosphatidylcholine with a high content of essential fatty acids from plant lecithins by adsorption of the phosphatides on aluminum oxide and extraction with alcohol. This process is characterized in that the raw oil phosphatides are dissolved in ethyl acetate or a dichlorinated hydrocarbon having 1 to 2 carbon atoms or in mixtures of these solvents. The solvent can contain up to 6% by volume of alcohol. The solution is then treated, with stirring, with at least five-fold amount of aluminum oxide relative to the content of raw phosphatide. Finally, the highly purified phosphatidylcholine is liberated with alcohol from the separated aluminum oxide. According to German Patent No. 1,617,680 the solution of the oily raw phosphatide solution is contacted with an aluminum oxide column (instead of stirring therewith) and the chemically pure phosphatidylcholine is liberated from the aluminum oxide adsorbent with alcohol.

Swiss Patent No. 561,088 and U.S. Pat. No. 2,945,869 describe purification processes to obtain soya phosphatide fractions to be used as emulsifiers for aliphatic emulsions designed for intravenous application. Alcoholic solutions of previously deoiled raw phosphatides are treated according to these processes with $Al_2O_3$, MgO or activated charcoal, respectively, in order to make these solutions poor in cephalin and, primarily to remove from these solutions most of the inositol-containing phosphatides which were found to lower the blood pressure in cats when introduced intravenously.

However, this latter process always requires a previous deoiling of the commercially available raw phosphatides prior to the preparation of the alcohol solutions which will only lead to a reduction in the cephalin content, regardless of the absorbent being used. A more extensive or complete removal of the cephalin cannot be accomplished by this known process.

German Patent No. 1,053,299 discloses a process to obtain natural choline phosphoric acid diglyceride esters which are free of colamin phosphoric acid diglyceride esters, by use of column chromatography where aluminum oxide is used, among other substances, as the absorbent. This process again uses an alcoholic extract of the previously deoiled raw phosphatide, with the prior deoiling accomplished by repeated extractions with acetone.

In the case of the processes disclosed by German Patent Nos. 1,617,679 and 1,617,680, the oily raw phosphatide mixtures are dissolved in ethyl acetate or a chlorinated hydrocarbon without prior deoiling, and these solutions are then treated with aluminum oxide. Deoiling of the raw phosphatides occurs while all phosphatides will remain at the adsorbent. The phosphatidylcholine can then be selectively liberated by treating the aluminum oxide with an alcohol. Highly purified oil-free phosphatidylcholines can be obtained by means of this process.

U.S. Pat. No. 3,798,246 discloses purifying the crude phosphatides recovered from soybean oil by contacting a hexane solution of the crude phosphatides with activated silica gel for at least 20 minutes, separating the silica gel from the solution, and evaporating the solvent.

U.S. Pat. No. 3,869,482 discloses a method for producing highly purified phosphatides from the total lipid extract of animal organs. The process comprises first completely freeing a total lipid extract of proteins by a solvent treatment. The extract is then washed to remove water soluble impurities and subjected to an absorption process for separating the other phosphorus-free lipoids.

U.S. Pat. No. 4,166,823 discloses a process for purifying phosphatides in order to obtain transparent phosphatides. The process involves subjecting crude phosphatides to the combined action of a hydrophobic liquid and water. The two liquids are separated and the purified phosphatide product is recovered from the hydrophobic liquid.

U.S. Pat. No. 4,235,793 discloses a process wherein raw lecithins are first extracted with a lower alcohol of 1 to 3 carbon atoms. The resulting two phases are separated and the alcohol-rich upper phase is treated with an aluminum oxide adsorbent. Elution of the adsorbent with an alcohol results in an oily phosphatidylcholine, free of cephalin and inositol phosphatides.

U.S. Pat. No. 4,443,378 discloses a process for the separation of acylated phospholipids. The process utilizes chromatography on silicic acid gel in a lower alkanol containing 1 to 4 carbon atoms as solvent and/or eluant.

U.S. Pat. No. 4,452,743 discloses a process for the separation of oil and/or phosphatidylethanolamine from alcohol soluble phosphatidylcholine products containing the same. This process also utilizes chromatography on silicic acid gel in a lower alkanol containing 1 to 4 carbon atoms as solvent and/or eluent.

U.S. Pat. No. 4,528,139 discloses a process for the preparation of phosphatide fractions highly enriched with phosphatidylcholine by warming an ethanolic extract of deoiled crude phosphatides at elevated temperatures before the addition of aluminum oxide and containing intensive stirring at elevated temperatures until the equilibrium saturation concentration is established.

Other publications which relate to the purification of phosphatidylcholine, phosphatide products or phosphatidylcholine products include British Patent No. 1,292,774; "Phosphatidylcholine Transfer Protein from Rat Liver: Purification and Radioimmunoassay" by Tuerlink et al *Method in Enzymology,* 1983, vol. 98, pp. 586–92; "Large Scale Purification of Phosphatidylcholine From Egg Yolk Phospholipids by Column Chromatography on Hydroglapatite." by Primes et al, *Journal of Chromatography,* 1982, vol. 236, No. 2, pp. 519–22; *Journal of Lipid Research,* 1977, vol. 18, No. 6, pp. 704–9; and, *Physiologie Vegetale,* "Rapid Preparation of Highly Purified Phosphatidylcholine By High-Performance-Liquid Chromatography" vol 24 No 5, (1986) pp. 597–605.

Generally, the processes described above result in fractions that are "enriched" in phosphatidylcholine rather than containing "purified" phosphatidylcholine in the context of being free of contaminating non-choline phosphatides. The costliness and efficiency of such processes depend upon the purity of the starting material. If a raw starting material is used, this may decrease the material cost of the process, but increase the actual processing cost because of the undesirable components. In general, the costliness of the present commercial process is high. New processes for the purification of phosphatidylcholine are therefore continuing to be developed in the hope of providing a process which is easier and more cost effective.

Therefore, it is an object of the present invention to provide a novel process for removing non-choline phosphatides from a raw material containing same which facilitates obtaining highly purified phosphatidylcholine.

Another object of the present invention is to provide a process for effectively obtaining a highly purified phosphatidylcholine product, particularly from a raw gum material.

It is another object of the present invention to provide such a process which is cost effective and easily manipulated.

These and other objects of the present invention will become apparent upon a review of the following description and the claims appended hereto.

SUMMARY OF THE INVENTION

In accordance with the foregoing objectives, provided is a process for removing non-choline phosphatides to facilitate obtaining a highly purified phosphatidylcholine product which is essentially free of non-choline phosphatides. The product can be obtained efficiently and effectively even when starting with a raw soybean gum (lecithin).

The process involves heating a lecithin product, e.g., a gum, liquid or granular product, which was obtained from animal or vegetable sources, such that non-choline phosphatides are degraded without substantially reducing the phosphatidylcholine content of the thermally-altered lecithin. Phosphatidylcholine can then be isolated in essentially pure form, free of non-choline phosphatides, from the thermally-altered lecithin. The separation/isolation can be achieved using a combination of conventional separation techniques.

A mixture of glycerides, e.g., triglycerides, diglycerides, free fatty acids, and in some cases monoglycerides, also results from the thermalization step, which mixture can be easily recovered by removal of acetone-insoluble components of the thermally-altered lecithin. The mono- and diglycerides, and free fatty acids, are a beneficial side product of the present invention and are generally produced by the thermalization step of the lecithin starting material. The non-choline phosphatides are believed to break down to give the mono- and diglycerides, and also free fatty acids. Depending on the starting material, the triglycerides and free fatty acids may be present prior to thermalization, and the latter may be released by thermalization of the phosphatides.

In a preferred embodiment, the lecithin is first thermally-altered by way of a heating step. Phosphatides are then precipitated from the thermally altered lecithin using a ketone solvent such as acetone. Phosphatidylcholine is then solubilized in an alcohol solvent, preferably ethanol. Final purification is achieved by passing the alcohol-soluble fraction through an alumina (aluminum oxide, $Al_2O_3$) column.

In another preferred embodiment, the ketone solvent is evaporated to provide a mixture of glycerides, e.g., triglycerides, diglycerides and monoglycerides, as well as free fatty acids. As discussed above, the glycerides and free fatty acids are a beneficial side product of the present invention and are generated by the thermalization step of the lecithin starting material. The non-choline phosphatides are believed to break down to give mono- and diglycerides, and other products.

The thermalization of the lecithin in fact permits one to use a very raw starting material, e.g., a gum which consists of crude hydrated phosphatides produced in the initial step of vegetable oil processing. The thermalization step breaks down the non-choline phosphatides not only to give the mixture of glycerides and fatty acids, but also to allow easy and quantitative separation of undesirable components from the desired phosphatidylcholine. This is done without substantially altering the fatty acid composition of the phosphatidylcholine. The thermalization step therefore is an essential feature of the present invention.

BRIEF DESCRIPTION OF THE DRAWING

The FIGURE of the Drawing provides an overall schematic of one preferred procedure of the process of the present invention.

DETAILED DESCRIPTION OF THE PREFERRED EMBODIMENTS

The starting material for the process of the present invention is lecithin. Lecithins are commercially available as a wide variety of products with an abundance of uses. For example, lecithin is available as (a) mixtures with vegetable oil, (b) fractionated forms that are enriched in a particular phosphatide, (c) modified forms that are chemically or enzymatically altered, and (d) others. The purest commercial bulk form of lecithin is granular at about 95–98% phosphatide. The variety of uses for lecithins include food additives, pharmaceuticals, cosmetics, animal feeds, paints and coatings, leather and textiles, magnetic tapes, plant protection products, and others. The surface active properties of lecithins are responsible for the wide variety of uses, particularly as emulsifiers.

One of the most recent and perhaps most important uses of lecithin is as the primary functional ingredient of liposomes which are single or multilaminar vesicules that are becoming increasingly important in the pharmaceutical industry as drug delivery vehicles, and in the cosmetics industry. The most efficacious and stable liposomes are formed with highly purified phosphatidylcholine preparations. For liposomes, 80 to 100% phosphatidylcholine is required for best results, particularly the hydrogenated form.

While any suitable, commercially available source of lecithin can be used, the effectiveness of the present invention permits one to use the rawest of forms, i.e., the gum.

The first step in processing crude oil extracted from plant seeds (e.g., soybean seeds) is the removal of phosphatides in a process called degumming. The gum fraction is composed mainly of hydrated phosphatides that are accompanied by a variety of other substances. The amount of vegetable oil present after removal of residual oil by centrifugation is about 5–10%, the water content according to the Karl Fisher procedure is 30 to 35%, and the bulk of the remaining materials is a mixture of phosphatides that includes mainly phosphatidylcholine, phosphatidylethanolamine, phosphatidylinositol and phosphatidic acid.

The method for thermalizing the lecithin generally involves a heating step. The thermalization is conducted under conditions of temperature, pressure and time sufficient to degrade the non-phosphatidylcholine phosphatides. The thermalization can involve heating, e.g., such as that disclosed in U.S. Pat. No. 5,008,037, which is hereby incorporated by reference. In a preferred embodiment, a thin-film evaporator (e.g., Pope Wiped-Film Still available from Pope Scientific, Inc. of Manomonee Falls, Wis.) is used as the reactor for the thermalization step and production of thermally-altered lecithin. The thin-film evaporator is preferred as it allows the desired thermalization to occur within a few seconds, with the amount of time varying based on the flow rate, at a temperature in the range of from about 150°–250° C., and more preferably about 200° C. When using gum as the starting material, the gum is generally first heated and diluted with a hydrocarbon solvent, such as hexane, to permit use in the thin-film evaporator.

Thin-film evaporators are commercially available and operate on the concept of heating a thin film of fluid. The evaporators generally comprise a heated body into which a fluid system is continuously fed. The fluid system is spread into a thin film by a rotating wiper blade assembly driven at a predetermined speed. The film, while being forced into turbulent flow by the wiper blades, progresses down through the inside body wall aided by gravity and slots in the wiper blades. While such systems are generally used for separation by evaporation, the system has been found to be quite successfully applicable for the thermalization of the present invention.

Phosphatidylcholine can then be recovered from the thermalized lecithin product. One important aspect of the present invention is the surprising discovery that phosphatidylcholine exists in a recoverable form subsequent to the thermalization. In previous studies on the browning reaction of lecithin by Fumie Tomioka and Takashi Kanaeda of the Department of Food Chemistry, Faculty of Agriculture, Tohoku University, Sendai, Japan, it was concluded that the browning products yielded by heating lecithin were polymerized compounds formed by an aldol condensation. Nevertheless, the present invention has surprisingly discovered that by thermalizing lecithin, a pure phosphatidylcholine product can be recovered from the thermalized product quite easily. In fact, the process of the present invention, by thermalizing lecithin, permits one to start with a very inexpensive product, e.g., a lecithin-containing gum, and quickly, efficiently and inexpensively separate out a pure phosphatidylcholine product from the raw starting material. The phosphatidylcholine can be readily isolated from the thermalized product using procedures which are known in the art.

FIG. 1 of the Drawing provides an overall schematic of one preferred procedure of the present invention. A lecithin-containing gum 1 is thermalized at 2 as discussed above. The preferred method of thermalization is one using a thin film evaporator as the thermalization occurs rapidly and safely. The resulting product is a thermally altered gum 3.

The thermally altered gum 3 is then subjected to a solvent precipitation step 4. A solvent employed is one that precipitates phosphatides, and especially phosphatidylcholine. Examples of preferred solvents are ketones, with acetone being the most preferred. The amount of solvent employed is generally in the range of about 20:1 to about 1:1 in volume of solvent (ml.) to weight of thermally altered gum (grams). A more preferred ratio is in the range of about 10:1 to 2:1 v (ml)/w (g), and most preferably a ratio of about 4:1 v/w.

The precipitated product, or the insoluble product B 6 contains the phosphatidylcholine. The precipitate is treated 7 with an alcohol containing mixture, with ethanol being the preferred alcohol. It is the alcohol, and in particular ethanol, which dissolves the phosphatidylcholine. The amount of alcohol employed is generally in the range of from about 20:1 to 1:1 volume of alcohol to weight of precipitate, more preferably in the range of 10:1 to 2:1 v (ml)/w (g), and most preferably about 6:1 v/w. The use of the alcohol produces an insoluble product C 8 and a soluble product D 9, which soluble product D includes the phosphatidylcholine.

The soluble product is then treated 10 using conventional methods to recover the pure phosphatidylcholine. Such methods can involve the use of a separation column, e.g., chromatography column of aluminum oxide. From the column, pure phosphatidylcholine can be recovered, which can be further purified by additional steps of treatment with ethanol and subsequent evaporation of the solvent. As shown in the following examples, the phosphatidylcholine recovered is quite pure, e.g., at least 98%.

The soluble product A 5 obtained from the solvent precipitation in 4 can also advantageously be treated to obtain a very useful product mixture. The soluble product A can simply be subjected to evaporation 12 in order to obtain a mixture 14 of glycerides, e.g., triglycerides, diglycerides and monoglycerides, and free fatty acids. This mixture has been found to be quite useful as an emulsifier.

In another embodiment of the present invention, the phosphatidylcholine can be recovered from the thermally altered gum using an emulsion separation. The emulsion separation can comprise adding to the thermally altered gum suitable solvents such as gasoline, followed by the addition of water and oil to create an emulsified mixture. Layers are created in the emulsified mixture, one a lighter color layer, and the other a darker colored layer. The darker colored layer is generally that of the solvent, such as gasoline, and is the top layer. This layer can simply be decanted off. The lower layer is generally a lighter colored layer and contains the phosphatidylcholine. This layer can be separated with the water removed by heating/evaporation. The recovered phosphatidylcholine product can then be treated with an alcohol such as ethanol in accordance with the procedure described above to recover the phosphatidylcholine, or, to ensure purity, recovered phosphatidylcholine product can be treated in accordance with the procedure described above beginning with the solvent precipitation step, e.g., using acetone.

Once the purified phosphatidylcholine is obtained using the process of the present invention, the product can be hydrogenated to produce the more commercially desirable fully saturated form of phosphatidylcholine. Conventional methods of hydrogenation can be used. The hydrogenated phosphatidylcholine is a white solid.

The following examples will help to illustrate the present invention. It should be noted, however, that the examples are not meant to be limitative, but only illustrative.

In the following examples, the following procedures were used.

Production of thermally-altered lecithin (gum) using the 6-inch Pope Thin-Film Evaporator (PTFE). The Pope thin-film evaporator is preheated and equilibrated to 200° C. The gum to be thermalized is heated at 100° C. for 1 hour, and then dissolved (suspended) in hexane (1.2:1 by vol.). The hexane solution of gum is placed into a feed flask of the evaporator preheated to 80° C. The wiper blades of the thin-film evaporator are turned on with the feed valve fully open such that the rate of production is 16–20 ml per minute. Thermally-altered gum (TBG) is collected in a beaker.

Phosphatidylcholine recovery

Acetone is added to the TBG (acetone/TBG ratio of about 4:1) and stirred for 1 hour at room temperature. The acetone-insoluble (AI) fraction is allowed to settle, and then separated from the acetone soluble (AS) fraction by decanting the liquid. Acetone is mixed with the AI fraction, collected and stirred for one-half hour at room temperature. The AS and AI fractions are separated as before. The above washing procedure is then repeated. The AI fraction is dried under a hood and stored at 5° C. The combined acetone washes (AS) are stored at 5° C. The solvent can be removed by rotary flash evaporation or by using the Pope-thin film evaporator.

To prepare the ethanol-soluble (ES) fraction, the AI fraction is dissolved in chloroform (optional) and poured into ethanol (95%). The chloroform step can be eliminated by dissolving the AI fraction in hot EtOH if desired. It is preferred to omit the use of chloroform. The solution is stirred for 10 minutes at room temperature and then centrifuged at 10,000 rpm for 10 minutes. The ethanol-insoluble (EI) and ethanol-soluble (ES) fractions are separated and stored at 5° C.

EXAMPLE 1

Five thousand (5000) grams of soybean gum (BG) were dissolved (suspended) in 6 liters of hexane. The BG had been centrifuged twice at 5000 rpm to remove excess oil, stored at 5° C. prior to use, and heated for 60 minutes at 100° C. prior to mixing with the hexane. Mixing was facilitated both by the heating and with stirring using a Lightnin Lab Master mixer equipped with a paddle blade. Thermally-altered gum was produced as a continuous flow at 16–20 ml per minute by using a 6 inch Pope Thin-Film Evaporator at 200° C. Approximately 84% of the gum was recovered as thermally altered gum.

The thermally-altered gum was separated into acetone-soluble (AS) and acetone-insoluble (AI) fractions by the aforedescribed usual procedure using 16.7 liters of acetone, yielding 44% and 56% of the total respectively. For quantitative purposes, 400 g of the AI fraction was processed further for the isolation and purification of PC.

The AI fraction was dissolved in 85% ethanol to produce the soluble (ES) and insoluble (EI) fractions, yielding 46% and 54% of the total, respectively. The AI was (optionally) first mixed with chloroform to facilitate dissolution. The EI fraction contained a black material. The ES fraction also possessed a dark color. The ES fraction was decolorized by passing it through a column of aluminum oxide ($Al_2O_3$). About 49% of the ES fraction was recovered by this procedure, and contained about 98% PC.

The remaining AI material from the 5000 grams of gum was processed as described above and about 540 grams of decolorized PC were obtained.

The composition of the thermally altered gum, as reflected in recovered fractions, is given in Table 1.

TABLE 1

Composition of Thermally-altered Soybean Gum

| Fractions | Major Fractions[1] | Component Fractions[2] |
| --- | --- | --- |
| Acetone soluble | 44.0 | |
| Triglycerides | | 40.7 |
| Diglycerides | | 31.6 |
| Monoglycerides[3] | | — |
| Free Fatty Acids[2] | | 27.8 |
| Acetone-insoluble | 56.0 | |
| Ethanol-insoluble | 30.2 | |
| Ethanol-soluble | 25.8 | |
| Decolored Ethanol-Soluble | 12.6 | |
| Triglycerides | | 0.1 |
| Diglycerides | | 0.6 |
| Monoglycerides | | — |
| Phosphatidylcholines | | 98.4 |
| Lysophosphadylcholines | | 0.9 |

[1]Values are weight percent of the original thermally altered gum starting material.
[2]Values are derived from high performance liquid chromatography (HPLC) analysis and are relative percentages of the components detected. Free acid content was determined by titration.
[3]Monoglycerides can be present in some preparations depending on thermalization conditions.

The fatty acid content of the recovered phosphatidylcholine was essentially unchanged by the thermalization process, as shown in Table 2.

TABLE 2

Fatty acid composition of hydrogenated and non-hydrogenated phosphatidylcholine isolated from thermally-altered soybean gum.

| | Relative Percent | | | |
| --- | --- | --- | --- | --- |
| Fatty Acids | Raw Gum | Thermalized Gum | PC | Hydrogenated-PC |
| $C_{16:0}$ | 21.4 | 16.7 | 15.0 | 32 |
| $C_{18:0}$ | 3.9 | 3.9 | 3.7 | 68 |
| $C_{18:1}$ | 10.0 | 14.2 | 9.9 | — |
| $C_{18:2}$ | 57.6 | 57.9 | 65.0 | — |
| $C_{18:3}$ | 7.2 | 7.2 | 6.4 | — |

Fatty acids were analyzed by gas-liquid chromatography (GLC) as their methyl derivatives after transesterification.

EXAMPLE 2

Phosphatidylcholine isolated from thermally-altered soybean gum (from Example 1) was hydrogenated using a Parr Reactor with a 300 ml capacity. One gram 5% Pd/C catalyst (1 g) and 30 ml hexane were placed in the reactor which was then purged with nitrogen gas for 10 minutes. The hydrogen ($H_2$) pressure was brought to 140 psi and 35° C. for 15 minutes. One gram (1 g) phosphatidylcholine was added to the reactor and the above steps were repeated. The reaction was allowed to proceed for 3 to 6 hours. Then, 100 ml hexane:ethanol (1:1 by vol) was added with the reaction mixture which was filtered at 50°–60° C. The solvent was removed from the filtrate by rotary flash evaporation leaving a white powder. The fatty acid components of the phosphatidylcholine were fully hydrogenated (saturated) by this procedure with palmitic ($C16:0$) and stearic ($C18:0$) acids as the fatty acid constituents of the hydrogenated product (Table 2).

Although the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. A process for obtaining purified phosphatidylcholine, which comprises
   (i) thermalizing a lecithin containing gum to thereby degrade substantially all non-choline phosphatides contained in the gum;
   (ii) precipitating phosphatides including phosphatidylcholine from the thermalized product with a ketone solvent;
   (iii) treating the precipitate with an alcohol solvent;
   (iv) passing the alcohol fraction through a separation column; and
   (v) recovering phosphatidylcholine from the column.

2. The process of claim 1, wherein the thermalization is achieved using a thin-film evaporator.

3. The process of claim 1, wherein the lecithin containing gum is a soybean gum.

4. The process of claim 1, wherein the ketone solvent in step (ii) is comprised of acetone.

5. The process of claim 1, wherein the alcohol solvent in step (iii) is comprised of ethanol.

6. The process of claim 1, wherein the separation column is an aluminum oxide column.

7. The process of claim 1, wherein the ketone solvent of step (ii) is recovered subsequent to the precipitation, with a mixture of glycerides and free fatty acids then being recovered by removal of the ketone solvent.

8. A process for obtaining purified phosphatidylcholine, which comprises (i) thermalizing a lecithin containing gum to degrade substantially all noncholine phosphatides contained in the gum; and (ii) recovering phosphatidylcholine by conducting an emulsion separation wherein the emulsion separation is comprised of adding gasoline, water and an oil to the thermalized product, allowing the layers to stratify, decanting off the top layer and recovering the bottom layer for recovery of phosphatidylchoine.

9. A process for obtaining purified phosphatidylcholine from a lecithin containing soybean gum, which comprises
   (i) thermalizing the lecithin containing material such that substantially all non-choline phosphatides are degraded;
   (ii) precipitating phosphatides including phosphatidylcholine from the thermalized product with acetone;
   (iii) treating the precipitate with ethanol;
   (iv) passing the ethanol fraction through a separation column; and,
   (v) recovering phosphatidylcholine from the column.

10. The process of claim 9, wherein the thermalizing is accomplished by a thin-film evaporator.

11. The process of claim 9, wherein the acetone solvent of step (ii) is recovered subsequent to the precipitation, with a mixture of glycerides and free fatty acids then being recovered by removal of the acetone solvent.

* * * * *